United States Patent [19]
Ramin et al.

[11] Patent Number: 5,882,635
[45] Date of Patent: Mar. 16, 1999

[54] COSMETIC COMPOSITION COMPRISING FILM-FORMING POLYMERS FOR APPLICATION TO A KERATINOUS SUBSTRATE

[75] Inventors: Roland Ramin, Itteville; Myriam Mellul, L'Hay-Les-Roses, both of France

[73] Assignee: L'Oreal, Paris, France

[21] Appl. No.: 815,846

[22] Filed: Mar. 12, 1997

[30] Foreign Application Priority Data

Mar. 13, 1996 [FR] France .................................. 96-03176

[51] Int. Cl.⁶ .................................................. A61K 7/043
[52] U.S. Cl. ............................................. 424/61; 424/401
[58] Field of Search ....................... 424/61, 401; 524/463

[56] References Cited

U.S. PATENT DOCUMENTS

| | | | |
|---|---|---|---|
| 4,301,046 | 11/1981 | Schlossman | 523/105 |
| 4,384,058 | 5/1983 | Galante | 524/32 |
| 4,421,881 | 12/1983 | Benkendorf et al. | 524/24 |
| 4,818,589 | 4/1989 | Johnson et al. | 428/201 |
| 5,008,105 | 4/1991 | Grollier et al. | 424/70.14 |
| 5,120,529 | 6/1992 | Koch et al. | |
| 5,571,858 | 11/1996 | de La Poterie et al. | |
| 5,578,297 | 11/1996 | Mellul et al. | 424/70.7 |
| 5,601,808 | 2/1997 | Mellul et al. | 424/61 |
| 5,603,939 | 2/1997 | Ser | 424/401 |
| 5,607,665 | 3/1997 | Calello et al. | 424/61 |
| 5,612,107 | 3/1997 | Sangani et al. | 428/41.7 |
| 5,616,598 | 4/1997 | Lion et al. | 514/374 |
| 5,639,447 | 6/1997 | Patel | 424/61 |
| 5,650,159 | 7/1997 | Lion et al. | 424/401 |
| 5,662,891 | 9/1997 | Martin | 424/61 |
| 5,667,768 | 9/1997 | Ramin | 424/61 |
| 5,672,647 | 9/1997 | Poterie et al. | 524/463 |
| 5,683,681 | 11/1997 | Ramin et al. | 424/61 |
| 5,725,866 | 3/1998 | Ramin | 424/401 |
| 5,753,211 | 5/1998 | Garson et al. | 424/61 |
| 5,804,169 | 9/1998 | Ramin | 424/61 |
| 5,807,540 | 9/1998 | Junino et al. | 424/61 |

FOREIGN PATENT DOCUMENTS

| | | |
|---|---|---|
| 230364 | 7/1987 | European Pat. Off. . |
| 391322 | 10/1990 | European Pat. Off. . |
| 627212 | 12/1994 | European Pat. Off. . |
| 661311 | 7/1995 | European Pat. Off. . |

*Primary Examiner*—Robert H. Harrison
*Attorney, Agent, or Firm*—Finnegan, Henderson, Farabow, Garrett & Dunner, L.L.P.

[57] ABSTRACT

The invention relates to a composition, in particular a cosmetic composition, to be applied to a keratinous substrate, comprising at least two incompatible film-forming polymers having surface tensions selected so as to form, after application, a laminated film. The invention also relates to the use of the polymers in a composition for obtaining a laminated film on a keratinous substrate.

20 Claims, No Drawings

COSMETIC COMPOSITION COMPRISING FILM-FORMING POLYMERS FOR APPLICATION TO A KERATINOUS SUBSTRATE

The present invention relates to a composition, in particular a cosmetic composition, to be applied to a keratinous substrate, comprising at least two film-forming polymers.

Generally, a nail varnish, in order to exhibit good cosmetic properties, must have good adhesion to the surface of the nail; the varnish film must be homogeneous and glossy and must exhibit a degree of flexibility while being resistant, for the purpose of preventing cracks and flaking off. In order to obtain such properties, it is necessary for the varnish film to be sufficiently soft, so as to be able to withstand deformations of the matrix of the nail and impacts. However, the film must also be sufficiently hard to prevent scratches and cracks and must also retain a degree of gloss.

This two-fold requirement is not generally fulfilled with conventional varnishes, which comprise a single film-forming polymer. One solution involves the use of a number of film-forming polymers as a mixture in the nail varnish composition.

European Patent Application No. EP-A-391,322 describes a nail varnish comprising a dispersion of polyurethane and acrylic resin. However, upon application of the varnish to the nail and after film forming, the two polymers form a homogeneous mixture (alloy) in the film obtained. This film exhibits cosmetic properties which are intermediate between those of the polymers of the mixture. Such a varnish therefore does not make it possible to obtain the best properties required or to benefit from the properties specific to each of the polymers.

The aim of the present invention is to provide a composition, in particular a cosmetic composition, capable of being applied on a keratinous substrate, which is able to provide a film which is simultaneously sufficiently soft and sufficiently hard and which exhibits good cosmetic properties.

A subject of the present invention is thus a composition capable of being applied to a keratinous substrate, which comprises a first film-forming polymer having a surface tension $Y_1$, similar to the surface tension of the substrate on which the composition is applied, and a second film-forming polymer having a surface tension $Y_2$, which is less than $Y_1$; the two polymers being incompatible with one another.

Another subject of the invention relates to the use, in a composition to be applied to a keratinous substrate, in particular in order to obtain a laminated film on the substrate, of a first film-forming polymer having a surface tension $Y_1$, similar to the surface tension of the substrate on which the composition is applied, and of a second film-forming polymer having a surface tension $Y_2$, which is less than $Y_1$; the two film-forming polymers being incompatible with one another.

The Inventors have discovered that, after application of the composition of the invention to a keratinous substrate and drying, a film composed of two laminated polymers is obtained. The first polymer constitutes the layer in contact with the keratinous substrate and the second polymer constitutes the layer in contact with the air. However, the separation between the two polymer layers is more or less distinct. Thus, "first polymer constituting the layer in contact with the keratinous substrate" is understood to mean that a majority of the first polymer, with respect to the second polymer, is in contact with the surface of the substrate. Similarly, the second polymer is mostly present in the second layer, which is in contact with the air. This distribution of the two polymers in the two layers does not rule out, for example, the presence or inclusion of the second polymer in the layer in contact with the substrate in which the first polymer is mostly present, or vice versa.

The composition according to the invention thus preferably constitutes a self-laminating composition.

In the laminated film, it is found that the layer in contact with the keratinous substrate exhibits good adhesion to the surface of the substrate and good flexibility; the upper layer in contact with the air exhibits good gloss, good hardness, good behavior towards wear and good resistance.

The composition according to the invention thus comprises at least two film-forming polymers which are incompatible with one another, each having specific surface tensions.

Surface tension of a polymer is understood to mean the surface tension of a dry film consisting solely of the polymer. Surface tension can be measured in particular according to the method of contact angles. This method involves the deposition of a drop of water and a drop of diiodomethane on a polymer film, the measurement of the angle formed by each drop with the film, and then the calculation of the surface tension of the film from the method described in "Double liaison [Double bond]", Chim. Peint., 82, Vol. 29, pages 263 to 268, the disclosure of which is incorporated herein by reference.

"Surface tension $Y_1$ similar to the surface tension of the substrate" is understood to mean a surface tension $Y_1$ such that: $0.9 \times Y_{substrate} \leq Y_1 \leq 1.1 \times Y_{substrate}$.

The first film-forming polymer having a surface tension $Y_1$, just like the second film-forming polymer having a surface tension $Y_2$, can be either a single polymer or a homogeneous mixture (that is to say, forming only a single phase in the dry film obtained with the mixture) of two or a number of polymers, the mixture then having a surface tension $Y_1$ or $Y_2$ respectively.

"Polymers incompatible with one another" is understood to mean polymers that form at least two different phases in the dry film obtained after application of the composition according to the invention. The polymers can be completely incompatible or partially incompatible with one another, that is to say that only a portion of the chain or chains of the first polymer may be incompatible with a portion of the chain or chains of the second polymer. When the polymers are completely incompatible, the separation of the two phases in the dry film is distinct. When the polymers are partially incompatible, the separation of the two phases in the dry film is indistinct.

The keratinous substrate can be, for example, a nail, an eyelash, an eyebrow, or hair.

When the keratinous substrate is the nail, $Y_1$ preferably ranges from 30 to 35 mJ/m², and $Y_2$, which is less than $Y_1$, preferably ranges from 22 to 32 mJ/m².

When the keratinous substrate is hair, an eyelash, or an eyebrow, $Y_1$ preferably ranges from 28 to 33 mJ/m², and $Y_2$ is less than $Y_1$, and preferably ranges from 22 to 32 mJ/m².

At least two of the polymers present in the composition according to the invention must be incompatible with one another, that is to say that they must form two different phases in the dry film obtained after application of the composition on the substrate.

The composition according to the invention may, preferably, comprise a third polymer, indeed a number of other polymers, with a surface tension $Y_3$ less than $Y_2$. This or these additional polymers are able to form other polymer layers superimposed on those formed by the first and second polymers according to the invention.

The film-forming polymers according to the invention are preferably selected from radical polymers, polycondensates, polymers of natural origin and their mixtures.

The radical polymers are preferably acrylic polymers and/or vinyl polymers. Mention is more preferably made, as a monomer carrying an anionic group which can be used in radical polymerization, of acrylic acid, methacrylic acid, crotonic acid, maleic anhydride and 2-acrylamido-2-methylpropanesulphonic acid.

The acrylic polymers can result from the copolymerization of monomers preferably selected from esters and/or amides of acrylic acid or of methacrylic acid. Mention is preferably made, as examples of monomers of ester type, of methyl methacrylate, ethyl methacrylate, butyl methacrylate, isobutyl methacrylate, 2-ethylhexyl methacrylate or lauryl methacrylate. Mention is preferably made, as examples of monomers of amide type, of N-t-butylacrylamide and N-t-octylacrylamide.

Use is more preferably made of acrylic polymers obtained by copolymerization of monomers containing ethylenic unsaturation containing hydrophilic groups, in particular of non-ionic nature, such as hydroxyethyl acrylate, 2-hydroxypropyl acrylate, hydroxyethyl methacrylate or 2-hydroxypropyl methacrylate.

The vinyl polymers can result from the homopolymerization or from the copolymerization of monomers preferably selected from vinyl esters, styrene and butadiene. Mention is more preferably made, as examples of vinyl esters, of vinyl acetate, vinyl neodecanoate, vinyl pivalate, vinyl benzoate and vinyl t-butylbenzoate.

The radical polymers according to the invention can also be substituted by halogen atoms and in particular by fluorine atoms.

According to the invention, the polycondensates are preferably selected from polyurethanes, polyesters, polyesteramides, polyamides, polyesters containing a fatty chain, epoxyester resins and their mixtures. The polyesters can be obtained, in a known way, by polycondensation of aliphatic or aromatic diacids with aliphatic or aromatic diols or with polyols. Use may preferably be made, as aliphatic diacids, of succinic acid, glutaric acid, adipic acid, pimelic acid, suberic acid or sebacic acid. Use may be preferably made, as aromatic diacids, of terephthalic acid or isophthalic acid or alternatively a derivative such as phthalic anhydride. Use may preferably be made, as aliphatic diols, of ethylene glycol, propylene glycol, diethylene glycol, neopentyl glycol, cyclohexanedimethanol or 4,4'-(1-methylpropylidene)bisphenol. Use may preferably be made, as polyols, of glycerol, pentaerythritol, sorbitol or trimethylolpropane.

The polyesteramides can be obtained in a manner analogous to the polyesters, by polycondensation of diacids with diamines or amino alcohols. Use may preferably be made, as diamine, of ethylenediamine, hexamethylene-diamine or meta- or para-phenylenediamine. Use may preferably be made, as amino alcohol, of monoethanolamine. Mention is preferably made, as a monomer carrying an anionic group which can be used in the polycondensation, for example, of dimethylolpropionic acid, trimellitic acid or a derivative such as trimellitic anhydride, the sodium salt of 3-sulphopentanediol acid or the sodium salt of 5-sulpho-1, 3-benzenedicarboxylic acid.

The polyesters containing a fatty chain can be obtained by the use during the polycondensation of diols containing a fatty chain.

The epoxyester resins can be obtained by polycondensation of fatty acids with a condensate containing $\alpha,\omega$-diepoxy ends. Such polymers are described in particular in K. Krishnamurti, Progress in Organic Coatings, 11 (1983), 167–197, the disclosure of which is incorporated herein by reference.

The polycondensates according to the invention can also be substituted by halogen atoms and in particular by fluorine atoms.

Mention may preferably be made, as polymers of natural origin, of shellac and sandarac gum.

According to the invention, the content on a dry basis of film-forming polymers preferably ranges from 5% to 50%, and more preferably ranges from 25% to 35%, by weight with respect to the total weight of the composition.

The mixture of film-forming polymers present in the composition is preferably composed, on a dry basis, of from 5% to 95%, and preferably from 30% to 80%, of a first film-forming polymer, and of from 5% to 95%, and preferably from 20% to 70%, of a second film-forming polymer. The mixture of film-forming polymers more preferably contains 50% of the first film-forming polymer and of 50% of the second film-forming polymer.

The composition according to the invention can also comprise, in addition to the film-forming polymers, plasticizers which make it possible to adjust the flexibility of the film without weakening its physical strength. The plasticizers which can be used are those commonly employed in nail varnish compositions. Mention may be made, as plasticizers, of dibutyl, dioctyl, diisobutyl and dimethoxyethyl phthalates; benzyl and glyceryl benzoates; triethyl and tributyl citrates or tributyl acetylcitrate; tributyl and triphenyl phosphates; glycols or camphor, as well as their derivatives and their mixtures. The plasticizers are preferably present in an amount ranging from 1% to 30% by weight with respect to the total weight of the composition.

In accordance with the invention, the film-forming polymers can be dissolved or dispersed in the medium of the composition. The cosmetically acceptable medium can comprise a solvent or of a mixture of solvents which are commonly used in nail varnish compositions. Mention may be made, as organic solvents, of ketones, such as acetone, methyl ethyl ketone and methyl isobutyl ketone; glycol ethers; alcohols, such as ethanol, n-butanol, n-propanol and isopropanol; acetates, such as butyl, ethyl and isopropyl acetate and 2-methoxyethyl acetate; linear and branched hydrocarbons, such as hexane and octane; and alternatively aromatic hydrocarbons, such as xylene and toluene. Use may also be made of water, alone or as a mixture with one or a number of solvents. Butyl and ethyl acetates are preferably used.

The composition according to the invention can also contain adjuvants commonly used in cosmetics. Mention may be made, as examples of adjuvants, of dyes, pigments, pearlescent agents, lakes, agents for combating UV radiation, thickening agents, fragrances, antifoaming agents, surface-active agents and bactericidal agents. Of course, the person skilled in the art will take care to choose this or these possible adjuvants, and/or their amount, so that the advantageous properties of the composition according to the invention are not, or not substantially, detrimentally affected by the envisaged addition.

When the composition is intended to be applied to the nails, it can be provided in the form of a nail varnish or of a nail care composition.

When the composition is intended to be applied to the eyelashes, it can be provided in the form of a mascara.

The composition according to the invention can also be used as a hair composition, which can be in the form of a shampoo, a conditioner, a hair setting composition, a fixing hair spray or a styling lotion.

The composition according to the invention can be packaged on its own in a bottle. It can also be packaged in two separate receptacles, each receptacle containing one of the first and second polymers.

Examples illustrating the present invention without, however, limiting it will now be given.

EXAMPLES

Example 1

A nail varnish having the following composition was prepared:

| | |
|---|---|
| Fluorinated resin as a 60% by weight solution in xylene, sold under the name "LUMIFLON LF 200" by the company ICI (First polymer; $y_1 = 35.7$ mJ/m$^2$) | 33.3 g |
| Polyurethane as a 25% by weight solution in a toluene/isopropanol/ketone mixture, sold under the name "DESMOLAC 4125" by the company BASF (Second polymer; $y_2 = 31$ mJ/m$^2$) | 33.3 g |
| Additives | 0.5 g |
| Solvent | q.s. for 100 g |

After application of the composition to the nail, a glossy, flexible and resistant film was obtained which existed in the form of two polymer layers.

Example 2

A nail varnish having the following composition was prepared:

| | |
|---|---|
| Fluorinated resin as a 60% by weight solution in xylene, sold under the name "LUMIFLON LF 200" by the company ICI (First polymer; $y_1 = 35.7$ mJ/m$^2$) | 25 g |
| Acrylic polymer as a 40% solution in xylene, sold under the name "NEOCRYL B 700" by the company ICI (Second polymer; $y_2 = 30.8$ mJ/m$^2$) | 37.5 g |
| Pigments | 1 g |
| Rheological additive | 1 g |
| Additives | 0.5 g |
| Solvent | q.s. for 100 g |

After application of the composition to the nail, a glossy, flexible and resistant film was obtained which existed in the form of two polymer layers.

We claim:

1. A composition for application to a keratinous substrate, comprising at least one first film-forming polymer having a surface tension $Y_1$ similar to the surface tension of said keratinous substrate to which said composition is applied and at least one second film-forming polymer having a surface tension $Y_2$ which is less than $Y_1$, wherein said at least one first film-forming polymer is incompatible with said at least one second film-forming polymer.

2. A composition according to claim 1, wherein said keratinous substrate is a nail.

3. A composition according to claim 2, wherein $Y_1$ ranges from 30 to 35 mJ/m$^2$ and $Y_2$ ranges from 22 to 32 mJ/m$^2$.

4. A composition according to claim 1, wherein said keratinous substrate is hair, an eyelash, or an eyebrow, and further wherein $Y_1$ is similar to the surface tension of said hair, said eyelash, or said eyebrow.

5. A composition according to claim 4, wherein $Y_1$ ranges from 28 to 33 mJ/m$^2$ and $Y_2$ ranges from 22 to 32 mJ/m$^2$.

6. A composition according to claim 1, wherein said at least one first film-forming polymer and said at least one second film-forming polymer are present in said composition in an amount, on a dry basis, ranging from 5% to 50% by weight with respect to the total weight of the composition.

7. A composition according to claim 6, wherein said at least one first film-forming polymer and said at least one second film-forming polymer are present in said composition in an amount, on a dry basis, ranging from 25% to 35% by weight with respect to the total weight of the composition.

8. A composition according to claim 1, wherein said at least one first film-forming polymer is present in an amount, on a dry basis, ranging from 5% to 95% by weight, and said at least one second film-forming polymer is present in an amount, on a dry basis, ranging from 5% to 95% by weight, with respect to the total weight of the film-forming polymers.

9. A composition according to claim 8, wherein said at least one first film-forming polymer is present in an amount, on a dry basis, ranging from 30% to 80% by weight, and said at least one second film-forming polymer is present in an amount, on a dry basis, ranging from 20% to 75% by weight, with respect to the total weight of the film-forming polymers.

10. A composition according to claim 1, wherein said at least one first film-forming polymer and said at least one second film-forming polymer are independently radical polymers, polycondensates, or polymers of natural origin.

11. A composition according to claim 10, wherein said radical polymers are acrylic polymers or vinyl polymers.

12. A composition according to claim 10, wherein said polycondensates are polyurethanes, polyesters, polyesteramides, polyamides, or epoxy-ester resins.

13. A composition according to claim 10, wherein said polymers of natural origin are shellac or sandarac gum.

14. A composition according to claim 1, wherein said composition further comprises at least one solvent, and wherein said at least one solvent is an organic solvent or water.

15. A composition according to claim 1, wherein said composition is in the form of a nail varnish or a nail care composition.

16. A composition according claim 1, wherein said composition is in the form of a mascara.

17. A composition according to claim 1, wherein said composition is in the form of a hair composition.

18. A method for preparing a composition for application to a keratinous substrate, said method comprising the step of including in said composition at least one first film-forming polymer having a surface tension $Y_1$ similar to the surface tension of said keratinous substrate to which said composition is applied and at least one second film-forming polymer having a surface tension $Y_2$ which is less than $Y_1$, wherein said at least one first film-forming polymer is incompatible with said at least one second film-forming polymer.

19. A method for obtaining a laminated film on a keratinous substrate, said method comprising the step of applying to said keratinous substrate a composition according to claim 1.

20. A method according to claim 18, wherein said composition is in the form of a nail varnish composition, a nail care composition, a mascara composition or a hair composition.

* * * * *